US010561747B1

(12) United States Patent
Ayyub et al.

(10) Patent No.: US 10,561,747 B1
(45) Date of Patent: Feb. 18, 2020

(54) MULTIFUNCTIONAL CANCER TARGETING NANOPARTICLES

(71) Applicant: KING SAUD UNIVERSITY, Riyadh (SA)

(72) Inventors: Faruq Mohammad Mohammad Ayyub, Riyadh (SA); Hamad A. Al-Lohedan, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/199,933

(22) Filed: Nov. 26, 2018

(51) Int. Cl.
 *A61K 49/18* (2006.01)
 *A61K 47/69* (2017.01)
 *A61K 31/704* (2006.01)

(52) U.S. Cl.
 CPC ........ *A61K 49/1863* (2013.01); *A61K 31/704* (2013.01); *A61K 47/6929* (2017.08)

(58) Field of Classification Search
 CPC ............ A61K 49/1863; A61K 47/6929; A61K 31/704
 See application file for complete search history.

(56) References Cited

U.S. PATENT DOCUMENTS

| 2010/0228237 A1 | 9/2010 | Chung et al. |
| 2016/0271274 A1 | 9/2016 | Ivkov |

OTHER PUBLICATIONS

Hassan, E.E. et al. "Optimized Formulation of Magnetic Chitosan Microspheres Containing the Anticancer Agent, Oxantrazole" Pharmaceutical Research, vol. 9, No. 3, 1992 (Year: 1992).*
"Conjugated definition" (https://en.oxforddictionaries.com/definition/conjugated) accessed Apr. 29, 2019 (Year: 2019).*
Mohammad, F. et al. "Doxorubicin-loaded magnetic gold nanoshells for a combination therapy of hyperthermia and drug delivery" Journal of Colloid and Interface Science 434 (2014) 89-97 (Year: 2014).*
Khademi, S. et al. "Folic acid-cysteamine modified gold nanoparticle as a nanoprobe for targeted computed tomography imaging of cancer cells" Materials Science & Engineering C 89 (2018) 182-193 (Year: 2018).*
Ding, Y. et al. "Synthesis of metallic nanoparticles protected with N,N,N-trimethyl chitosan chloride via a relatively weak affinity" Nanotechnology 17 (2006) 4156-4162 (Year: 2006).*
Faruq Mohammad, "Influence of Gold Nanoshell on Hyperthermia of Superparamagnetic Iron Oxide Nanoparticles," Journal of Physical Chemistry (114) pp. 19194-19201 (2010).
Faruq Mohammad "Doxorubicin-loaded Magnetic Gold Nanoshells for a Combination Therapy of Hyperthermia and Drug Delivery," Journal of Colloid and Interface Science (434) pp. 89-97 (2014).
Paula I. P. Soares, "Application of Hyperthermia for Cancer Treatment: Recent Patents Review," Recent Patents on Anti-Cancer Drug Discovery (7) pp. 64-73 (2012).
G. Ali Mansoori, "A Comparative Study of Two Folate-Conjugated Gold Nanoparlicles for Cancer Nanotechnology Applications," Cancers (2) pp. 1911-1928 (2010).
Jessica M. Rosenholm, "Targeted Intracellular Delivery of Hydrophobic Agents Using Mesoporous Hybrid Silica Nanoparticles as Carrier Systems," Nano Letters 9(9) pp. 3308-3311 (2009).
Jie Lu, "Biocompatibility, Biodistribution, and Drug-Delivery Efficiency of Mesoporous Silica Nanoparticles for Cancer Therapy in Animals," Small 6(16) pp. 1794-1805 (2010).
Chunfang Zhou, "Release of Folic Acid in Mesoporous NFM-1 Silica," Journal of Nanoscience and Nanotechnology (10) pp. 7398-7401 (2010).
Alfonso Garcia-Benett, "In Search of the Holy Grail: Folate-Targeted Nanoparticles for Cancer Therapy," Biochemical Pharmacology (81) pp. 976-984 (2011).
Hamidreza Kheiri Manjili, "D, L-Sulforaphane Loaded Fe3O4@ Gold Core Shell Nanoparticies: A Potential Sulforaphane Delivery System," PLOS One pp. 1-20 (2016).

* cited by examiner

*Primary Examiner* — Andrew S Rosenthal
(74) *Attorney, Agent, or Firm* — Richard C. Litman; Nath, Goldberg & Meyer

(57) ABSTRACT

Multifunctional cancer targeting nanoparticles include a magnetic central core including gold coated iron oxide, an outer layer including trimethyl chitosan microspheres and folic acid and a linker between the central core and the outer layer, the linker including cysteamine. An anti-cancer drug can be supported by the outer layer. The multifunctional cancer targeting nanoparticle can provide simultaneous cancer cell diagnosis and therapy. An amount of heat and an amount of the anti-cancer drug released by the nanoparticle can be controlled by application of a magnetic field.

11 Claims, 5 Drawing Sheets

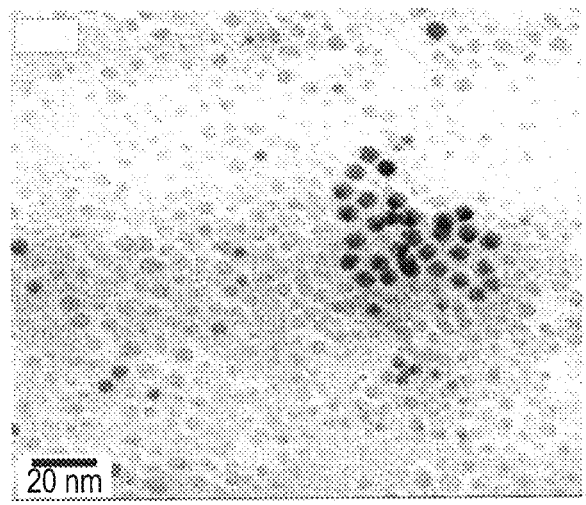
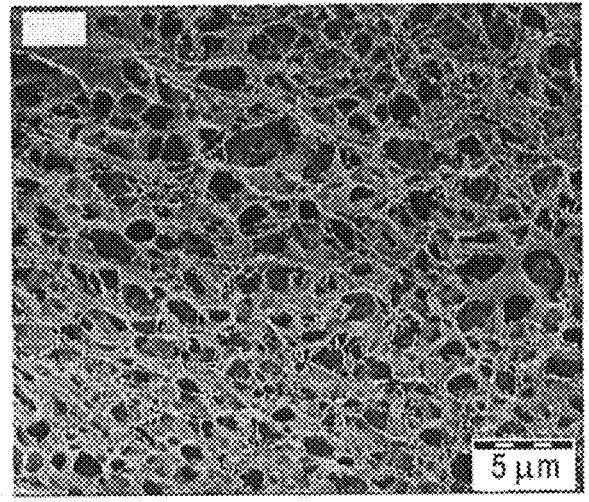
FIG. 1A      FIG. 1B
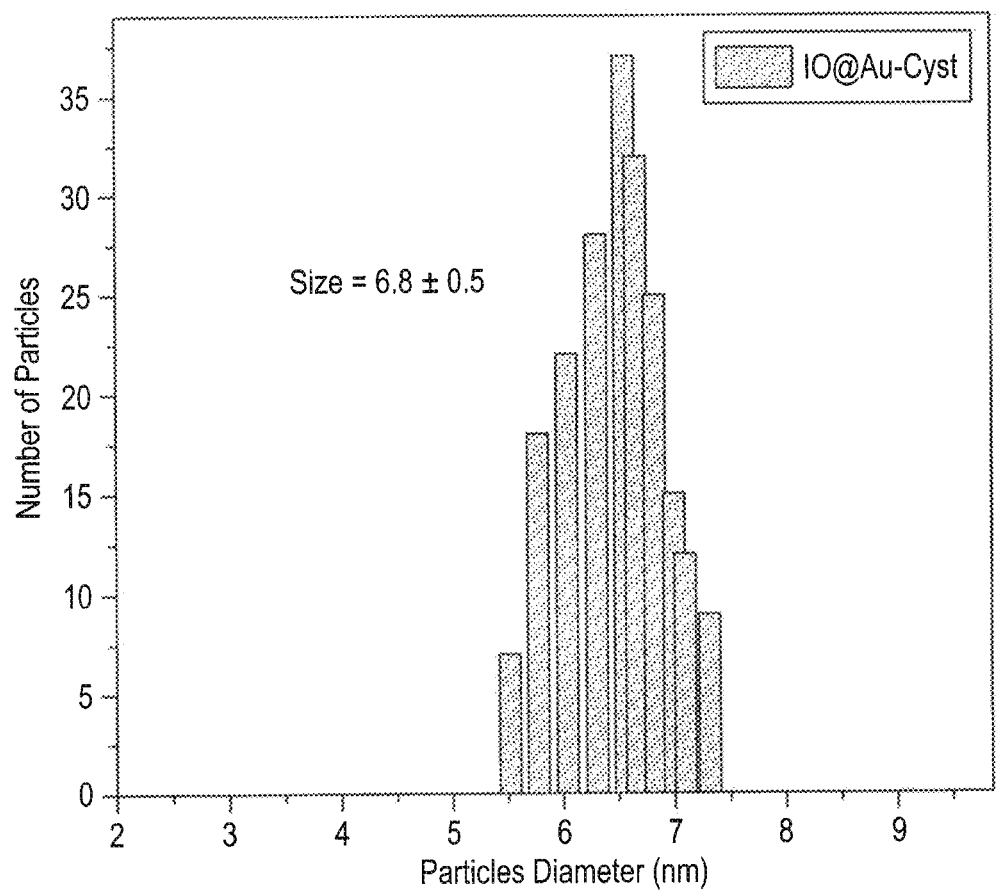
FIG. 2

MULTIFUNCTIONAL CANCER TARGETING NANOPARTICLES

BACKGROUND

1. Field

The disclosure of the present patent application relates to nanotechnology, and particularly to multifunctional cancer targeting nanoparticles.

2. Description of the Related Art

Traditional cancer treatments include surgery, chemotherapy, and radiation. Surgery is effective for treatment of some isolated, solid cancers, but cannot be used in all cases. Chemotherapy kills rapidly dividing cells indiscriminately, resulting in significant side effects. Radiation can be targeted to a particular region of the patient's body; however, it cannot be targeted specifically at cancerous cells lying deep inside the body, resulting in undesired side effects due to damage to healthy tissues and it cannot be used in all cases. To overcome these issues, the medical research community has focused on developing targeted therapies.

Recent developments in cancer treatment have focused on targeted therapies, such as monoclonal antibody therapies. Monoclonal antibodies may be used to target cancer treatment by either driving the innate immune response to attack cancerous cells, or by acting as a targeted delivery mechanism for a conjugated drug (such as a traditional chemotherapy drug). However, monoclonal antibodies specific to cancerous cells are difficult to develop as the cell surface markers used by cancerous cells are also commonly found on non-cancerous cells.

In addition to their other limitations, these traditional and targeted treatments are mono-functional. Nanotechnology has sought to provide multifunctional tools for cancer therapy. As nanoparticles may be labelled with multiple active groups, they may form the basis of multifunctional cancer treatments. Thus, nanoparticles have the potential to be used in theranostics, using diagnostic imaging to confirm diagnosis and then triggering release of one or more targeted anti-cancer active agents. However, significant challenges remain with regard to optimizing biocompatibility, biodistribution, bioavailability, targeting, and drug release.

Thus, multifunctional cancer targeting nanoparticles capable of cancer cell diagnosis and treatment solving the aforementioned problems are desired.

SUMMARY

Multifunctional cancer targeting nanoparticles include a magnetic central core including gold coated iron oxide, an outer layer including trimethyl chitosan microspheres and folic acid and a linker between the central core and the outer layer, the linker including cysteamine. An anti-cancer drug can be supported by the outer layer. The multifunctional cancer targeting nanoparticles can provide simultaneous cancer cell diagnosis and therapy. An amount of the anti-cancer drug released by the nanoparticles can be controlled by application of a magnetic field.

The multifunctional cancer targeting nanoparticles (MCTNPs) demonstrate cancer cell targeting capacity, combined with high magnetization values, allowing for diagnostic uses such as Magnetic Resonance Imaging (MRI), targeted, triggered release of an anti-cancer drug, and hyperthermia treatment.

These and other features of the present disclosure will become readily apparent upon further review of the following specification and drawings.

BRIEF DESCRIPTION OF THE DRAWINGS

FIG. 1A is a high-resolution transmission electron microscopy scan showing the size of the multifunctional cancer targeting nanoparticles.

FIG. 1B is a field-emission scanning electron microscopy scan of the surface morphology of the multifunctional cancer targeting nanoparticles.

FIG. 2 is a graph of the particle diameter of the multifunctional cancer targeting nanoparticles.

Similar reference characters denote corresponding features consistently throughout the attached drawings.

DETAILED DESCRIPTION OF THE PREFERRED EMBODIMENTS

Figure 6:
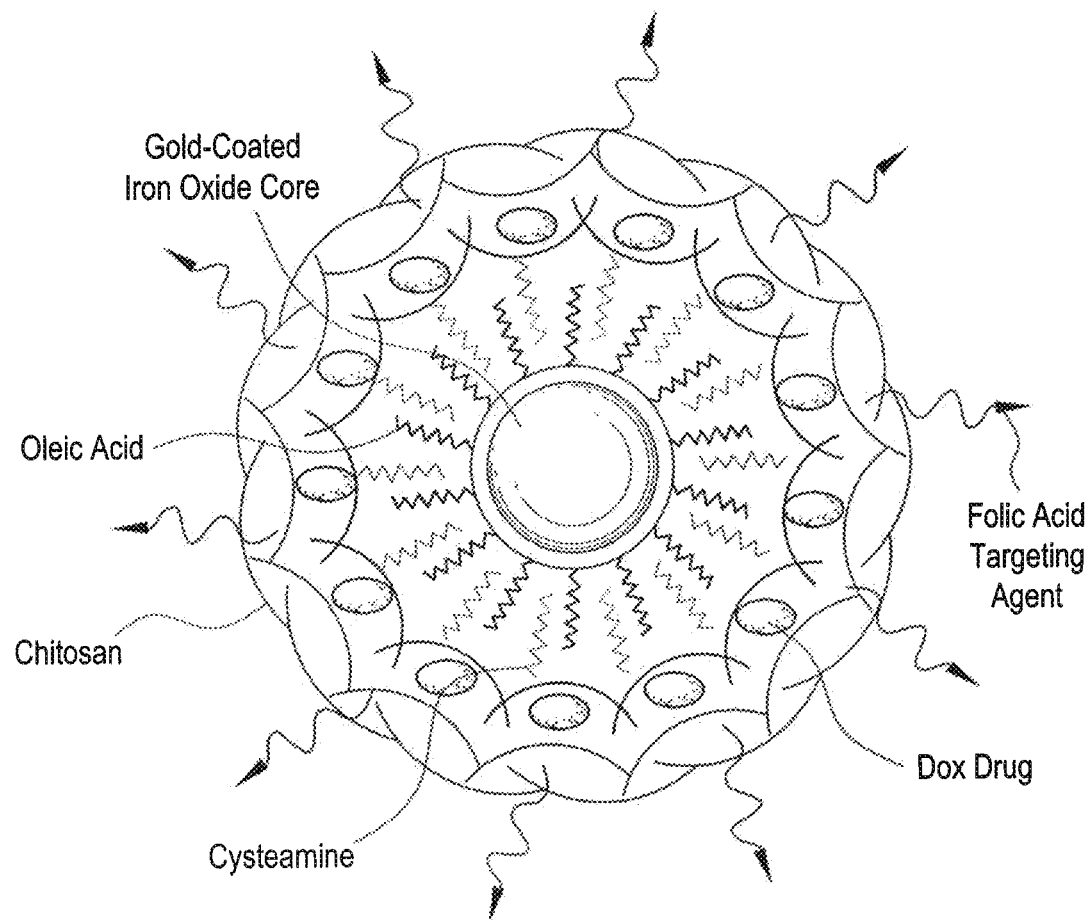
FIG. 6 is a schematic diagram of a multifunctional cancer targeting nanoparticle.

Multifunctional cancer targeting nanoparticles (MCTNPs) are capable of cancer cell diagnosis and treatment. Referring to FIG. 6, a multifunctional cancer targeting nanoparticle can include a magnetic central core including gold coated iron oxide, an outer layer including trimethyl chitosan, e.g., trimethyl chitosan microspheres, and folic acid, and a linker between the central core and the outer layer. The linker can include cysteamine. An anti-cancer drug can be supported by the outer layer. The MCTNPs can be spherical and monodispersed. The MCTNPs can be uniformly distributed with a mean size distribution of about 6.8 nm. The MCTNPs can be porous.

The MCTNPs demonstrate cancer cell targeting capacity, combined with high magnetization values, allowing for diagnostic uses such as Magnetic Resonance Imaging (MRI), targeted release of an anti-cancer drug, and hyperthermia treatment. Broad subsets of cancer cells significantly overexpress the folate receptor in order to scavenge additional folic acid. Accordingly, the folic acid labelled MCTNPs can be preferentially transported into cancer cells via folate receptor mediated endocytosis. The gold coated iron oxide core provides a superparamagnetic core with enhanced magnetization values. This allows the MCTNPs to act as a magnetic contrast agent, which can be detected via traditional means, such as a MRI. In addition, the MCTNPs may cause targeted hyperthermia when exposed to an external oscillating magnetic field. The chitosan protects the gold coated iron oxide core from the oxidative environment, and improves drug loading capacity. This allows the MCTNPs to offer up to a 100% anti-cancer drug release rate. Thus, the MCTNPs may act as triggered delivery vectors for anti-cancer drugs, such as Doxorubicin.

A method for synthesizing MCTNPs can include forming a colloidal suspension of iron oxide nanoparticles and reacting the suspension with diphenyl ether, 1,2 hexadecanediol, oleic acid, oleyamine, and gold acetate to provide magnetic gold coated iron oxide nanoparticles. The magnetic gold coated iron oxide nanoparticles can then be mixed with a cysteamine solution and separated to form surface-modified magnetic gold coated iron oxide nanoparticles. These nanoparticles can then be mixed with chitosan, e.g., methylated chitosan microspheres, to produce encapsulated, surface-modified gold coated iron oxide nanoparticles. These nanoparticles are then reacted with 1-ethyl-3(3-dimethylaminopropyl) carbodiimide (EDC) and folic acid to provide the multifunctional cancer targeting nanoparticles.

The following examples illustrate the present teachings.

Example 1

Synthesis of MCTNPs

Iron oxide particles were formed by mixing iron acetylacetonate with diphenyl ether, oleic acid and oleylamine under inert atmosphere with vigorous stirring. 1,2 hexadecanediol was added to this mixture and heated to around 210° C. with reflux for two hours maintaining oxygen free conditions. The reaction mixture was cooled to room temperature and then degassed ethanol was added to precipitate a black colored product. The precipitate was separated by centrifugation. The separated precipitated product was then washed with a series of solvents starting with hexane, followed by a mixture of hexane and ethanol, and finally with ethanol. The product was dispersed in ethanol, separated magnetically, and dried to obtain a black powder of iron oxide particles which were dispersed in toluene, forming a colloidal suspension of iron oxide nanoparticles.

For synthesizing magnetic gold coated iron oxide nanoparticles, a solution mixture including diphenyl ether, 1,2 hexadecanediol, oleic acid, oleylamine and gold acetate was added under inert atmosphere to the colloidal suspension of 10 nanoparticles. This reaction mixture was heated to around 190° C. with reflux for about 1.5 hours. After cooling to room temperature, ethanol was added and a dark purple precipitate was separated by centrifugation. The precipitate was re-suspended in hexane, washed with ethanol between two and three times and dried. The particles were then suspended in ethanol and magnetic separation was used to separate magnetic gold coated iron oxide nanoparticles from non-magnetic gold particles and any unwanted carbon mass produced from oleic acid/oleylamine used during the reaction.

The magnetic gold coated iron oxide nanoparticles were surface modified with cysteamine. The magnetic gold coated iron oxide nanoparticles were suspended in toluene and thoroughly agitated, e.g, by shaking. In a separate flask, an equal volume of cysteamine hydrochloride in distilled water was prepared. The nanoparticle solution and the cysteamine solution were mixed together and stirred for about ten minutes. Initially, this resulted in two distinct phases, the bottom being a colorless aqueous phase, and the top being the purple toluene phase with the suspended nanoparticles. After about three to four hours of rest, the magnetic nanoparticles migrated into the aqueous phase. Magnetic gold coated iron oxide nanoparticles surface modified with cysteamine were then separated using a magnetic separator, washed between two and three times with distilled water, and dried under an inert atmosphere.

For the methylation of chitosan, chitosan, sodium iodide, iodomethane, and an aqueous solution of sodium hydroxide were mixed with N-methyl-2-pyrrolidinone and stirred on a water bath until a clear solution was formed. The reaction mixture was heated to 60° C. for an hour by refluxing with a Liebig condenser. The reaction mixture was then cooled to room temperature and the product was separated by precipitation with ethanol and isolated by centrifugation. The product was washed with diethyl ether and ethanol, and dried to obtain methylated chitosan powder with a degree of quaternization about 46% (as observed from NMR spectroscopy). The methylated chitosan polymer was then converted to microspheres by crosslinking with sodium tripolyphosphate. This step included mixing methylated chitosan suspended in distilled water dropwise with tripolyphosphate in distilled water. The mixture was stirred for an hour and the product was precipitated by adding ethanol followed by centrifugation. The product was then lyophilized to obtain a powder of methylated chitosan microspheres.

The methylated chitosan microspheres were then mixed with distilled water to produce a concentration of 10 mg/mL. Equal volumes of magnetic gold coated iron oxide nanoparticles with cysteamine and methylated chitosan microspheres were mixed dropwise with stirring for one hour. A tripolyphosphate cross linker (at 2 mg/mL in distilled water) was added dropwise to the mixture and stirring continued for another 8 hours to form a stable suspension of surface modified magnetic gold coated iron oxide nanoparticles encapsulated with chitosan. These nanoparticles were separated by centrifugation, washed with distilled water, and dried under an inert atmosphere to provide the nanoparticles in powdered form.

The powdered nanoparticles were then suspended in distilled water to form a solution. This solution was added to 1-theyl-3-(3-dimethylaminopropyl) carbodiimide suspended in distilled water and sonicated for three minutes. FA was dissolved in distilled water and added to the reaction mixture, which was stirred in a chiller for about two hours, maintaining a constant temperature of 4° C. to provide the multifunctional cancer targeting nanoparticles. The resulting nanoparticles were separated by centrifugation, and washed multiple times with distilled water.

An aqueous solution of Doxorubicin hydrochloride in distilled water was added dropwise to a colloidal dispersion of the multifunctional cancer targeting nanoparticles, while stirring. The mixture was allowed to stir for about 16 hours, allowing partitioning of the drug into the chitosan, cysteamine and oleic acid/oleylamine layer surrounding the gold coated iron oxide core. The resulting multifunctional cancer targeting nanoparticles loaded with Doxorubicin were separated from the reaction solution using a magnet, washed with distilled water, dried, and stored.

Example 2

Characterization of MCTNPs

Nanoparticles from various stages of Example 1 were tested to characterize their size, morphology, specific magnetization, heat and drug release under applied magnetic fields, and toxicity to two specific cancer cell lines.

High Resolution Transmission Electron Microscopy (FIG. 1A) and Field-Emission Scanning Electron Microscopy (FIG. 1B) demonstrated that the particles are monodispersed with a spherical shape and an average size of 6.8 nm (FIG. 2). The surface morphology confirms the porous nature resulting from the chitosan, affording improved drug loading characteristics. These figures also confirm that this method results in monodispersed nanoparticles of a uniform size and shape.

Figure 3:
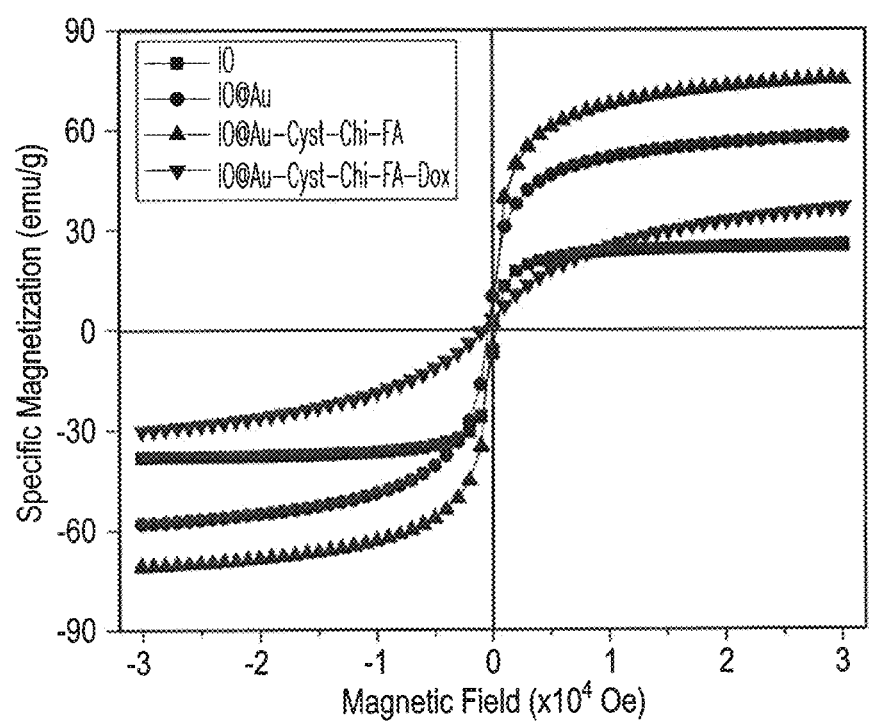
FIG. 3 is a graph of the magnetic hysteresis curves for iron oxide nanoparticles, gold-coated iron oxide nanoparticles, the multifunctional cancer targeting nanoparticles without anti-cancer drug loaded therein, and multifunctional cancer targeting nanoparticles loaded with anti-cancer drug.

Magnetization studies were performed using the iron oxide nanoparticles, magnetic gold coated iron oxide nanoparticles, magnetic gold coated nanoparticles with cysteamine, chitosan, and folic acid, and magnetic gold coated nanoparticles with cysteamine, chitosan, folic acid, and Doxorubicin (FIG. 3). The MCTNPs had higher magnetization values before loading the Doxorubicin. However, even the Doxorubicin loaded MCTNPs had increased magnetization when compared to iron oxide nanoparticles. This property can be desirable for cancer treatment and diagnostics, e.g., MRI, hyperthermia, and drug delivery.

Figure 4A:
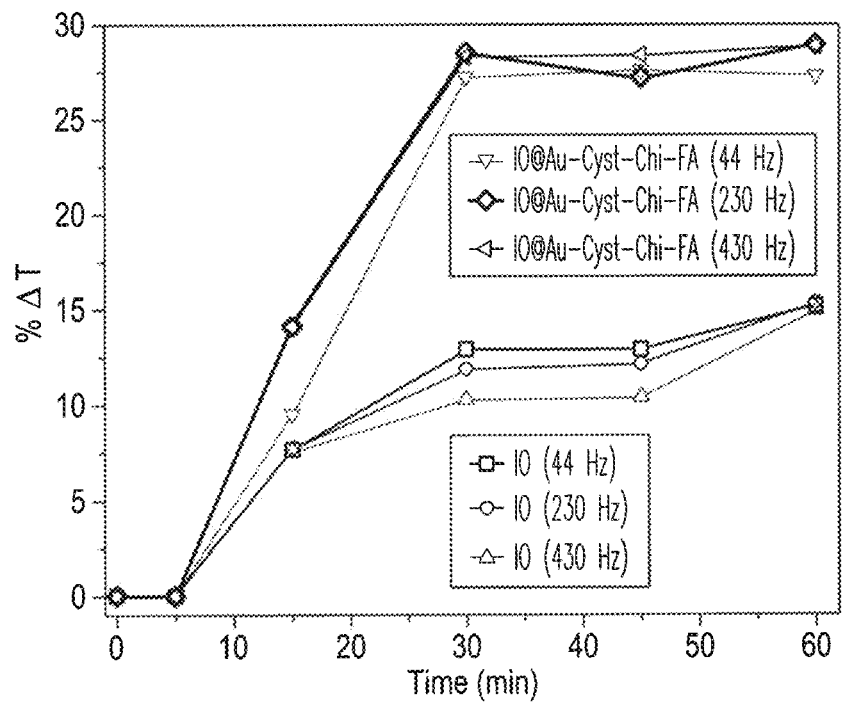
FIG. 4A is a graph of heat release effects of control and multifunctional cancer targeting nanoparticles in response to different applied magnetic fields.
Figure 4B:
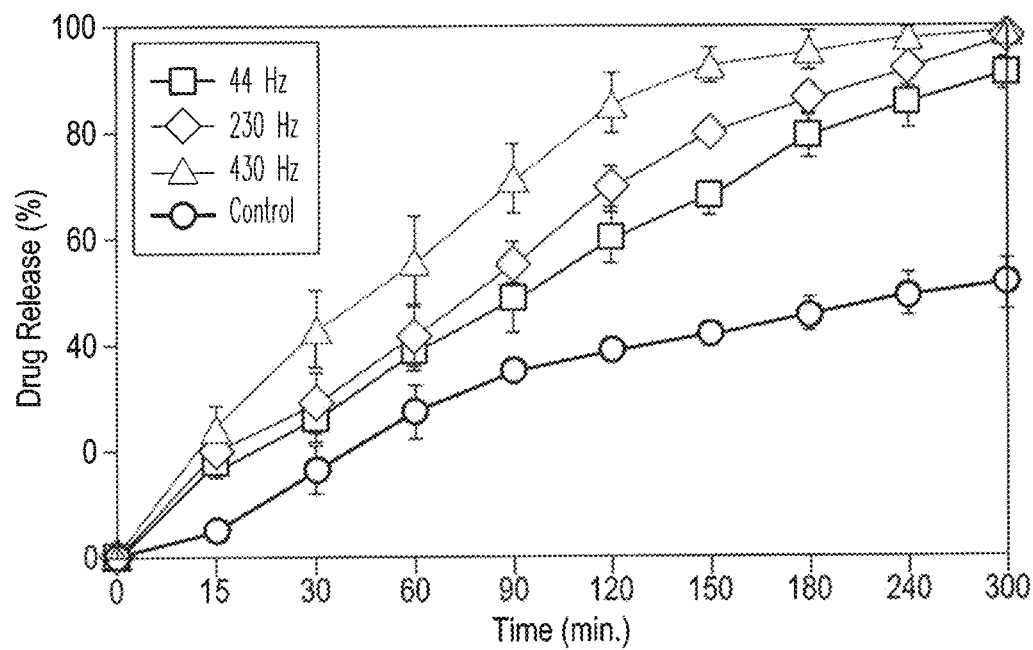
FIG. 4B is a graph of the anti-cancer drug release of the multifunctional cancer targeting nanoparticles in response to different applied magnetic fields.

Studies of heat release (FIG. 4A) and Doxorubicin release (FIG. 4B) demonstrated that application of an external magnetic field to the MCTNPs can trigger heat release and drug release. Thus, heat and drug release can be externally controlled. The MCTNPs were able to release higher amounts of heat than their core particles, e.g., pure iron oxide particles. At each frequency, the total amount of heat released by the MTCNs is almost three times higher than the corresponding iron oxide particles. In addition cysteamine bonding increase the water dispersible behavior by incorporating hydrophilic groups at the surface. Similarly, drug release from the MCTNPs loaded with Doxorubicin increased with an increase in amount of applied magnetic field (Hz).

Figure 5A:
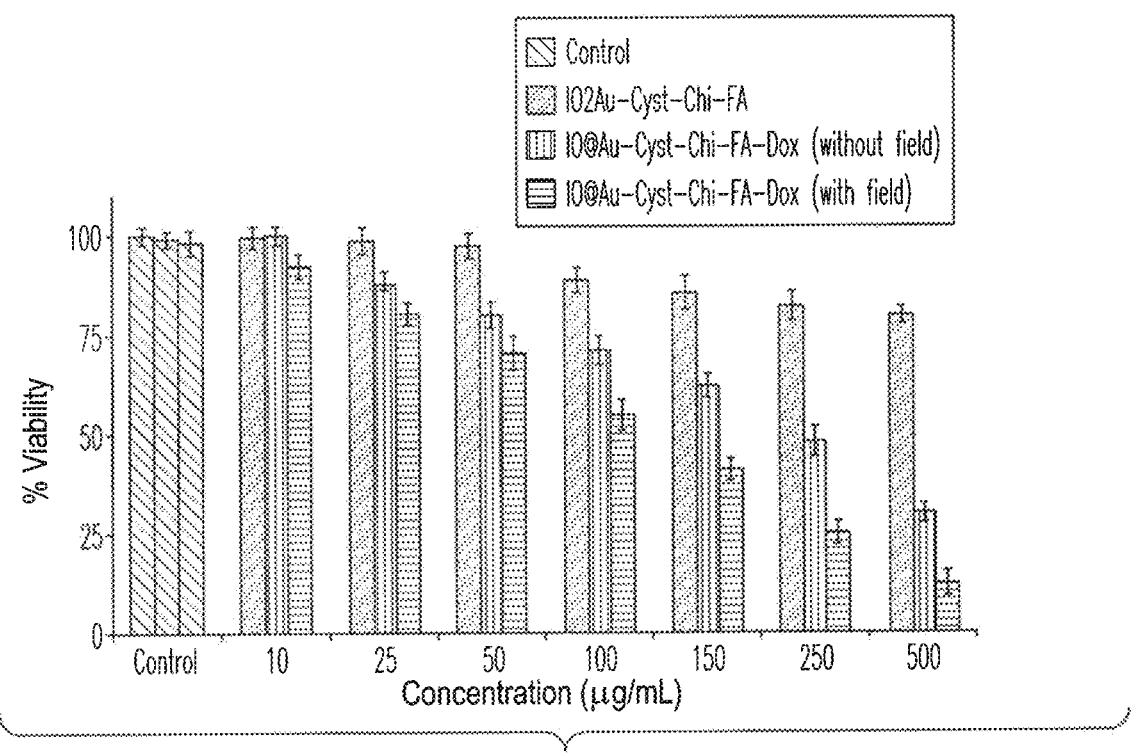
FIG. 5A is a graph of the effect of control, multifunctional cancer targeting nanoparticles without anti-cancer drug, and multifunctional cancer targeting nanoparticles loaded with anti-cancer drug, with and without a 430 Hz magnetic field, upon MCF-7 cancer cell viability.
Figure 5B:
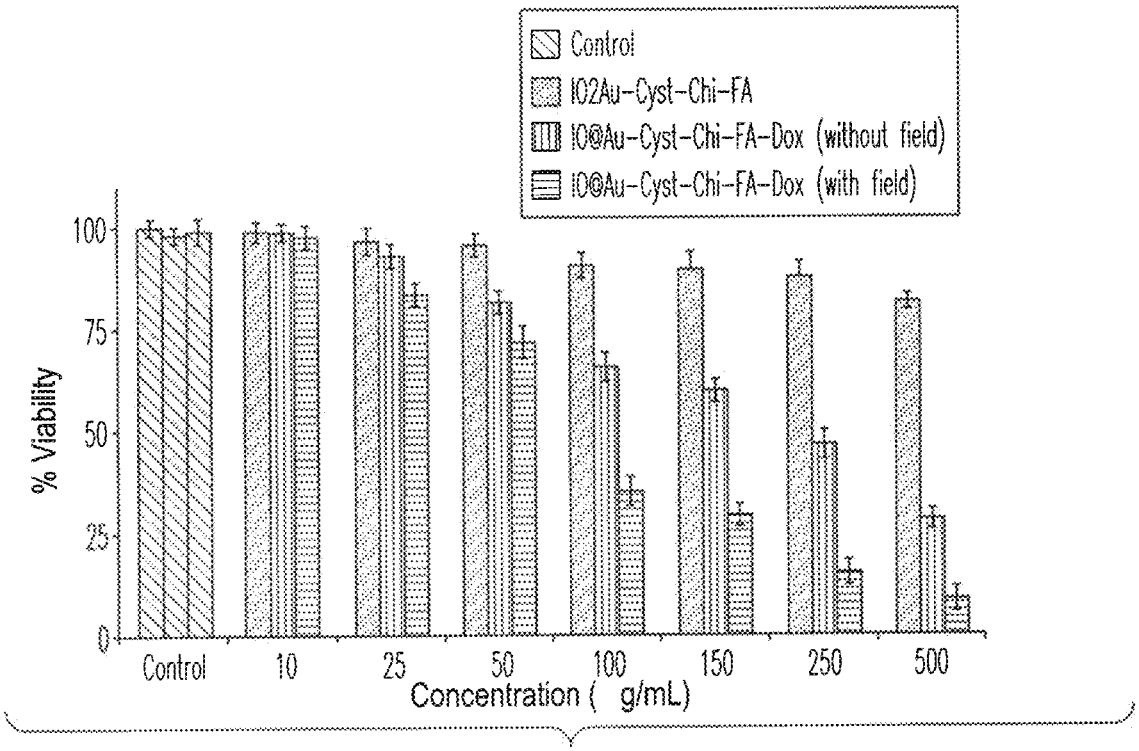
FIG. 5B is a graph of the effect of control, multitunctional cancer targeting nanoparticles without anti-cancer drug, and multifunctional cancer targeting nanoparticles loaded with anti-cancer drug, with and without a 430 Hz magnetic field, upon MDA-MB2 cancer cell viability.

External control of toxicity or amount of drug to be released at the targeted cells was confirmed by measuring viability of two cancer cell lines (MCF-7 and MDA-MB2) treated with MCTNPs without anti-cancer drug (magnetic gold coated nanoparticles with cysteamine, chitosan, and folic acid) and MCTNPs with Doxorubicin (magnetic gold coated nanoparticles with cysteamine, chitosan, folic acid, and Doxorubicin) in the absence of an external magnetic field; and MCTNPs without anti-cancer drug (magnetic gold coated nanoparticles with cysteamine, chitosan, and folic acid) and MCTNPs with Doxorubicin (magnetic gold coated nanoparticles with cysteamine, chitosan, folic acid, and Doxorubicin in the presence of a magnetic field) (See FIG. 5A for MCF-7 and FIG. 5B for MDA-MB2). The results confirmed that the extent/mechanism of cell death can be externally controlled. The MCTNPs can provide treatment in three stages: simple hyperthermia, drug delivery, and a combination of both. Simple hyperthermia can cause apoptosis in cancer cells, the Doxorubicin drug delivery can cause apoptosis in cancer cells, and the combination of both can cause the cancer cells to undergo direct necrosis, which means that this mode of treatment can be employed for cancer cells during the progression/termination stages. All of the three modes can be externally controlled, e.g., how much heat released at the tumor targeted site, amount of drug released to the tumor, and when both hyperthermia and drug delivery are employed simultaneously, the cancer cells can be drawn to direct necrosis without any reversal.

It is to be understood that the magnetic nanoparticle probe with multiple functions of cancer cell diagnosis and treatment is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. Multifunctional cancer targeting nanoparticles, comprising:
   a magnetic central core including gold coated iron oxide nanoparticles, wherein the iron oxide is reacted with diphenyl ether, 1,2 hexadecanediol, oleic acid, oleylamine, and gold acetate to provide the magnetic gold coated iron oxide nanoparticles, further wherein an average particle size of the nanoparticles is 6.8 nm;
   an outer layer including trimethyl chitosan microspheres and folic acid, wherein the chitosan microspheres are formed by crosslinking methylated chitosan with sodium tripolyphosphate to provide the methylated chitosan microspheres;
   a linker between the central core and the outer layer, the linker including cysteamine; and
   an anti-cancer drug supported by the outer layer.

2. The multifunctional cancer targeting nanoparticles of claim 1, wherein the anti-cancer drug comprises Doxorubicin.

3. The multifunctional cancer targeting nanoparticles of claim 1, wherein the nanoparticles are porous.

4. A method of synthesizing the multifunctional cancer targeting nanoparticles of claim 1, comprising:
   providing a colloidal suspension of iron oxide nanoparticles;
   reacting the colloidal suspension with diphenyl ether, 1,2 hexadecanediol, oleic acid, oleylamine, and gold acetate to provide magnetic gold coated iron oxide nanoparticles;
   mixing the magnetic gold coated iron oxide nanoparticles with cysteamine to provide surface-modified magnetic gold coated iron oxide nanoparticles;
   mixing the surface-modified magnetic gold coated iron oxide nanoparticles with methylated chitosan microspheres to encapsulate the surface-modified magnetic gold coated iron oxide nanoparticles with the methylated chitosan microspheres; and
   conjugating the encapsulated, surface-modified magnetic gold coated iron oxide nanoparticles with folic acid to provide the multifunctional cancer targeting nanoparticles.

5. The method of synthesizing multifunctional cancer targeting nanoparticles according to claim 4, further comprising loading an anticancer drug into the multifunctional cancer targeting nanoparticle.

6. The method of synthesizing multifunctional cancer targeting nanoparticles according to claim 5, wherein the anticancer drug is Doxorubicin.

7. The method of synthesizing multifunctional cancer targeting nanoparticles according to claim 4, wherein the iron oxide nanoparticles are formed by:
   mixing iron acetylacetonate with diphenyl ether, oleic acid, and oleylamine under inert atmosphere with stirring to form a first mixture;
   adding 1,2 hexadecanediol to the first mixture and heating to about 210° C. with reflux for about two hours under oxygen free conditions to form a heated mixture;
   cooling the heated mixture to room temperature;
   adding degassed ethanol to the cooled mixture to provide a precipitate; and isolating the precipitate to provide the iron oxide nanoparticles.

8. The method of synthesizing multifunctional cancer targeting nanoparticles according to claim 4, wherein the surface-modified magnetic gold coated iron oxide nanoparticles are formed by:
   suspending the magnetic gold coated iron oxide nanoparticles in toluene to provide a nanoparticle solution;
   preparing an equal volume of cysteamine hydrochloride in distilled water to provide a cysteamine solution;
   mixing the nanoparticle solution and the cysteamine solution for about ten minutes to form a mixture;
   resting the mixture for about three to four hours to provide the surface-modified magnetic gold coated iron oxide nanoparticles.

9. The method of synthesizing multifunctional cancer targeting nanoparticles according to claim 4, wherein the methylated chitosan microspheres are produced by:
   mixing chitosan, sodium iodide, iodomethane, and an aqueous solution of sodium hydroxide with N-methyl-2-pyrrolidinone to provide a chitosan solution;
   stirring the chitosan solution on a water bath until a clear solution forms;
   heating the chitosan solution to around 60° C. by refluxing to form a heated solution;
   cooling the heated solution to provide a methylated chitosan in the solution;
   forming the methylated chitosan into a methylated chitosan powder; and
   crosslinking the methylated chitosan powder with sodium tripolyphosphate to provide the methylated chitosan microspheres.

10. The method of synthesizing multifunctional cancer targeting nanoparticles according to claim 4, wherein the step of mixing the methylated chitosan microspheres with the surface-modified magnetic gold coated iron oxide nanoparticles comprises:
    mixing the methylated chitosan microspheres with distilled water at a concentration of about 10 mg/mL;
    mixing equal volumes of magnetic gold coated nanoparticles with the methylated chitosan microspheres dropwise with stirring to form a mixture;
    adding a tripolyphosphate cross linker dropwise to the mixture;
    stirring the mixture for about eight hours; and
    isolating the nanoparticles from the mixture.

11. The method of synthesizing multifunctional cancer targeting nanoparticles according to claim 4, wherein conjugating the encapsulated, surface-modified magnetic gold coated iron oxide nanoparticles with folic acid comprises the steps of:
    adding 1-ethyl-3(3-dimethylaminopropyl) carbodiimide suspended in distilled water to the encapsulated, surface-modified magnetic gold coated iron oxide nanoparticles and sonicating for about three minutes to form a sonicated mixture; and
    adding folic acid dissolved in distilled water to the sonicated mixture and stirring in a chiller for about two hours to form the multifunctional cancer targeting nanoparticles.

\* \* \* \* \*